(12) United States Patent
Morita

(10) Patent No.: US 9,727,964 B2
(45) Date of Patent: Aug. 8, 2017

(54) IMAGE PROCESSING DEVICE

(71) Applicant: SHIMADZU CORPORATION, Kyoto-shi, Kyoto (JP)

(72) Inventor: Hisanori Morita, Kyoto (JP)

(73) Assignee: SHIMADZU CORPORATION, Kyoto (JP)

(*) Notice: Subject to any disclaimer, the term of this patent is extended or adjusted under 35 U.S.C. 154(b) by 10 days.

(21) Appl. No.: 14/909,485

(22) PCT Filed: Aug. 8, 2013

(86) PCT No.: PCT/JP2013/071562
§ 371 (c)(1),
(2) Date: Feb. 2, 2016

(87) PCT Pub. No.: WO2015/019474
PCT Pub. Date: Feb. 12, 2015

(65) Prior Publication Data
US 2016/0171693 A1 Jun. 16, 2016

(51) Int. Cl.
*G06K 9/00* (2006.01)
*G06T 7/00* (2017.01)
(Continued)

(52) U.S. Cl.
CPC ............ *G06T 7/0014* (2013.01); *A61B 6/469* (2013.01); *A61B 6/5258* (2013.01); *G06T 5/002* (2013.01);
(Continued)

(58) Field of Classification Search
CPC ..... G06T 7/0012; G06T 5/002; G06T 7/0014; G06T 5/50; G06T 11/60;
(Continued)

(56) References Cited

U.S. PATENT DOCUMENTS 6,904,163 B1 6/2005 Fujimura et al.
8,908,832 B2 12/2014 Yamashita
(Continued)

FOREIGN PATENT DOCUMENTS

JP 01-314477 12/1989
JP 8-248541 9/1996
(Continued)

OTHER PUBLICATIONS

PCT/JP2013/071562, International Search Report mailed Sep. 3, 2015, 5 pages—Japanese, 2 pages—English.
(Continued)

*Primary Examiner* — Jonathan S Lee
(74) *Attorney, Agent, or Firm* — Andrew F. Young, Esq.; Lackenbach Siegel, LLP

(57) ABSTRACT

This image processing device operates by identifying a region that is in a similar image and has a pattern which is the same as a pattern appearing in a section of a reference image, and repeating an operation several times and the section and the region are superposed to generate a reduced-noise fragment, after which the reduced-noise fragments obtained for all of the regions of the reference image are combined to generate a reduced-noise image. When such an operation actually is attempted with an image processing device the regions corresponding to the sections in the reference image cannot be found from the similar image. Therefore, with the present invention the reduced-noise fragments are generated by performing spatial processing on the sections. Thus, reduced-noise fragments can be obtained reliably for all of the regions of the reference image, and noise can be removed from the reference image more reliably.

7 Claims, 17 Drawing Sheets

(51) Int. Cl.
   *A61B 6/00* (2006.01)
   *G06T 5/00* (2006.01)
   *G06T 11/60* (2006.01)
   *G06T 5/50* (2006.01)

(52) U.S. Cl.
   CPC ............... *G06T 5/50* (2013.01); *G06T 11/60* (2013.01); *G06T 2207/10016* (2013.01); *G06T 2207/10116* (2013.01); *G06T 2207/10121* (2013.01); *G06T 2207/20021* (2013.01); *G06T 2207/20221* (2013.01)

(58) Field of Classification Search
   CPC . G06T 2207/10016; G06T 2207/10116; G06T 2207/10121; G06T 2207/20021; G06T 2207/20221; A61B 6/469; A61B 6/5258
   See application file for complete search history.

(56) References Cited

U.S. PATENT DOCUMENTS

| | | | |
|---|---|---|---|
| 8,983,029 B2 | 3/2015 | Hasegawa | |
| 9,125,619 B2 | 9/2015 | Yabugami | |
| 2006/0066736 A1* | 3/2006 | Tsuruoka | H04N 5/367 348/241 |
| 2007/0196031 A1* | 8/2007 | Chen | G06K 9/40 382/278 |
| 2008/0123979 A1* | 5/2008 | Schoner | G06T 5/002 382/242 |
| 2011/0019935 A1* | 1/2011 | Kelm | G06T 5/50 382/275 |
| 2013/0223712 A1* | 8/2013 | Kobayashi | G06T 11/003 382/131 |
| 2014/0301625 A1* | 10/2014 | Takahashi | A61B 6/5258 382/132 |
| 2015/0281572 A1* | 10/2015 | Pongratz | G06K 9/0063 348/207.1 |
| 2016/0267638 A1* | 9/2016 | Segall | H04N 19/86 |

FOREIGN PATENT DOCUMENTS

| | | |
|---|---|---|
| JP | 11-353464 | 12/1999 |
| JP | 2001078996 | 3/2001 |
| JP | 2010-114474 | 5/2010 |
| JP | 2010-183386 | 8/2010 |
| WO | WO 2013/042352 | 3/2013 |
| WO | WO 2014/181383 | 11/2014 |

OTHER PUBLICATIONS

U.S. Appl. No. 14/759,353, filed Jul. 6, 2015, Okuno.
U.S. Appl. No. 14/785,758, filed Oct. 20, 2015, Sakimoto.
U.S. Appl. No. 14/784,528, filed Oct. 24, 2015, Okuno.
U.S. Appl. No. 13/719,032 filed Dec. 18, 2012, Takahasi.
U.S. Appl. No. 13/995,872, filed Aug. 20, 2013, Kogame.
U.S. Appl. No. 14/157,120, filed Jan. 16, 2014, Okamura.
U.S. Appl. No. 14/363,345, filed Jul. 15, 2014, Ishikawa.
U.S. Appl. No. 14/416,412, filed Jan. 22, 2015, Ishikawa.
U.S. Appl. No. 14/668,354, filed Mar. 25, 2015, Tanaka.
U.S. Appl. No. 14/754,056, filed Jun. 29, 2015, Tanaka.
U.S. Appl. No. 14/760,152, filed Jul. 9, 2015, Tanaka.
U.S. Appl. No. 14/798,991, filed Jul. 14, 2015, Shirota.
U.S. Appl. No. 14/830,187, filed Aug. 19, 2015, Kawabe.
U.S. Appl. No. 14/764,018, filed Jul. 28, 2015, Kakio.
U.S. Appl. No. 14/785,737, filed Oct. 20, 2015, Watanabe.
U.S. Appl. No. 14/766,522, filed Aug. 7, 2015, Okuno.

* cited by examiner

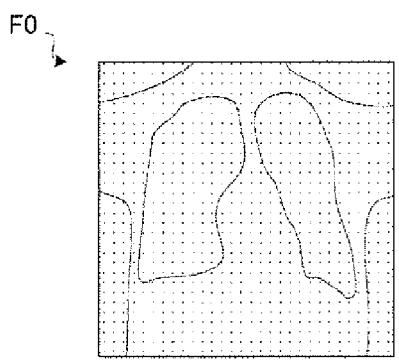 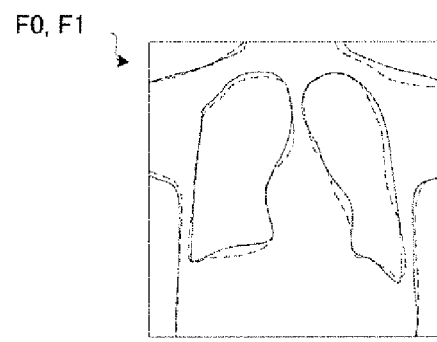
*FIG. 3A*   *FIG. 3B*

Search Area Setting Processing

*FIG. 6A* *FIG. 6B*
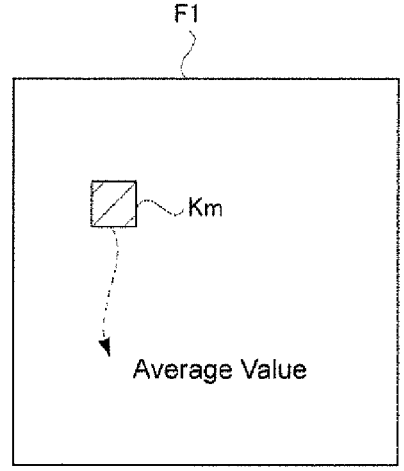
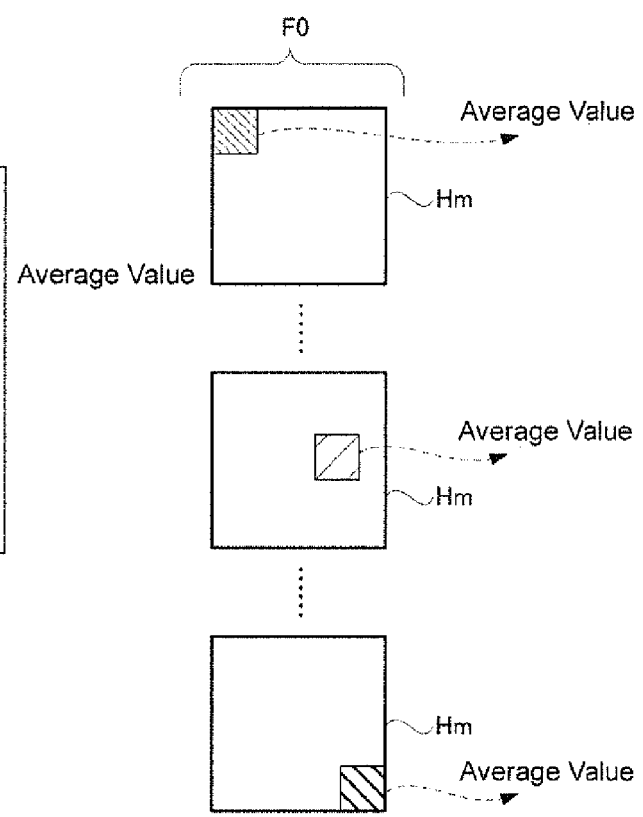

In the case of existing of Rm corresponding to Km

In the case of noon-existing of Rm corresponding to Km

*FIG. 10*

| Generation of F0 | | |
|---|---|---|
| Generation of F1 | Generation of F1α based on F0, F1 | First time |
| Generation of F2 | Generation of F2α based on F1, F2 | Second time |
| Generation of F3 | Generation of F3α based on F2, F3 | Third time |
| ⋮ | | |
| Generation of Fn | Generation of Fnα based on Fn-1, Fn | n times |

*FIG. 12*

| K1 | W(H1) |
|----|-------|
| K2 | W(H2) |
| K3 | W(H3) |
| K4 | W(H4) |

⋮

*FIG. 14A*        *FIG. 14B*
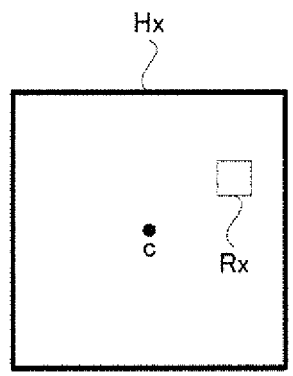 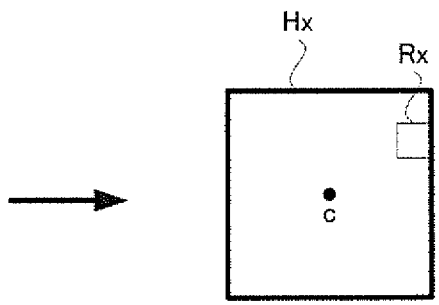

*FIG. 17*

| Generation of F0 | | |
|---|---|---|
| Generation of F1 | Generation of S1α based on F0, F1 | First time |
| Generation of F2 | Generation of S2α based on F1, F2 | Second time |
| Generation of F3 | Generation of S3α based on F2, F3 | Third time |
| ⋮ | | |
| Generation of Fn | Generation of Snα based on Fn, Sn-1 | n times |

IMAGE PROCESSING DEVICE

CROSS REFERENCE TO RELATED APPLICATIONS

This application relates to and claims priority from Ser. No.: PCT/JP2013/071562 filed Aug. 8, 2013, the entire contents of which are enclosed herein by reference.

FIGURE SELECTED FOR PUBLICATION

FIGS. 1(A) and 1(B)

BACKGROUND OF THE INVENTION

Field of the Invention

The present invention relates to an image processing device to eliminate noise superimposed on the radiation image and particularly relates to an image processing device so as to improve quality of the image of each frame constituting a live image.

Description of the Related Art

A medical facility equips a radiation imaging device to acquire the radiation image. Some radiographic devices can continuously image the radiation image and then output the results as a video. Such video can be called as a live image (e.g., refer to Patent Document 1.)

Since irradiation of low-dose radiation to the subject is used to provide the live image, the S/N ratio thereof is inferior to the S/N ratio for static imaging (spot imaging) and a lot of noises are included therein. The radiographic device equips an image processing device so as to reduce such noise. Such image processing device can structurally provide the noise reduction image having the S/N ratio improved by superimposing two continuous frames with time.

However, the live image is a video catching the movement of the subject. Accordingly, the image processing by which the two continuous frames are simply superimposed may provide a noise reduction image of which the subject images are as if doubled. Because the incorporated position and shape of the subject are different each other between frames. In addition, since the level of misalignment between the subject's images per se varies depending on the portion of the frame, even if one frame is just shifted relative to another frame to superimpose, doubling of the images cannot be prevented.

Thus, according to the conventional constitution, a structure so as to improve such defect has been adopted. Specifically, the frames are superimposed while confirming conformity of the subject images relative to each portion of the frame. The inventor specifically sets forth the correction method thereof. Here, one frame (first frame) out of two frames is segmented to fine blocks and one of the blocks is noticed. A pattern indicating a part of the subject image is incorporated into the noticed block. This pattern is called as a notice pattern.

Here, another frame (second frame) is considered. The second frame is almost the same image but not exactly the same image as the first frame. Specifically, the notice pattern relative to the first frame has moved to somewhere on the image with regard to the second frame. Conversely, the area incorporating the notice pattern on the first frame must be somewhere on the second frame. Such area has the same shape and size as the notice block of the first frame but the occupying position on the frame is not guaranteed to be always the same between frames.

According to the conventional image processing device, the area incorporating the same pattern as the notice pattern on the notice block of the first frame is searched out from the second frame and then those patterns are superimposed each other and the superimposition processing relative to the notice block is accomplished. The image processing device executes the same superimposition processing relative to all blocks on the first frame and generates one noise reduction image by connecting the superimposition results acquired at this time (e.g., refer to Patent Document 2.)

PRIOR ART

Patent Document

Patent Document 1: JP Patent Published H11-335267 A
Patent Document 2: JP Patent Published 2001-078996 A*

Aspects and Summary of the Invention

Nevertheless, there is following problems to be solved as for the conventional image processing device.

Specifically, it is not guaranteed whether the noise reduction image can be absolutely acquired by using the conventional image processing.

According to the conventional image processing device, when the area incorporating the same pattern as the notice pattern on the notice block of the first frame is searched out from the second frame, such search area is limited. Specifically, according to the conventional image processing device, the search area is designated on the second frame and the notice pattern is searched within such search area. At this time, according to the conventional image processing device, if the notice pattern could not be retrieved within the search area, the measures for such case has not been fully considered.

It is deemed that the search area, where the notice pattern is searched, should be just set broadly to prevent the state in which the notice pattern could not be retrieved. Certainly, if the search area is broaden, the risk, in which the notice pattern is not found from the second frame, can be reduced. However, the broader the search area is, the more the burden to the image processing device increases. According to the conventional image processing device that processes the live image, it is premised on that the noise reduction image is generated every frame acquisition. If the burden for generation-processing of the noise reduction image is high, the generation of the noise reduction image by the image processing device delays and would be too late to image the live image.

Following such circumstances, the purpose of the present invention is to provide an image processing device that can suppress the burden and can conduct absolutely the image processing.

Means for Solving the Problem

The present invention comprises the following system to solve the above problem.

Specifically, an image processing device of the present invention comprises; (A) a block setting means that sets a part of the reference image incorporating a fluoroscopic image of the subject as a block; (B) a search are setting means that sets a search area in the similar image, wherein the position of the subject being incorporated is different from the position thereof in the reference image; (C) an area specifying means that specifies the area having the same pattern on the similar image as the pattern of the subject, being incorporated in the block of the reference image; (D) a noise reduction fragment generation means that generates the noise reduction fragment, wherein the noise components incorporated in the block and the area are offset each other by superimposing the area specified by the area specifying means on the similar image and the block of the reference image; and (E) a noise reduction image generation means that generates the noise reduction image, wherein the noise component being incorporated in the reference image is reduced by that the block setting means connects the noise reduction fragments relative to each block set all over the reference image; (D+) wherein the noise reduction fragment generation means generates the noise reduction fragment by executing the spatial processing relative to the block when the area specifying means fails specify the area.

[Action and Effect] Basically, the image processing device of the present invention is operative to specify the area having the same pattern on the similar image as the pattern of the subject being incorporated into a block of the reference image; to repeat multiple times the operation of generation of a noise reduction fragment by superimposing the block and the area so that the noise reduction fragments can be acquired all over the reference image; and to generate the noise reduction image by connecting these. Eventually, if the image processing device would be operated in such way, the incident in which an area corresponding to the block on the reference image cannot be found out takes place. Thus, the present invention is operative to generate the noise reduction fragments by executing a spatial processing relative to the block when the area having the same pattern as the pattern of the subject being incorporated into a block of the reference image cannot be found out on the similar image. In this way, the noise reduction fragments can be absolutely acquired from all over the reference image so that the image processing device capable of eliminating further absolutely the noise from the reference image can be provided.

Further, according to the image processing device having (D+), as described above, it is further preferable that the spatial processing executed by the noise reduction fragment generation means is a smoothing processing.

[Action and Effect] The above constitution illustrates the specific constitution of the image processing device of the present invention. If the spatial processing executed by the noise reduction fragment generation means is a smoothing processing, the noise reduction fragments can be acquired further absolutely.

In addition, according to the image processing device of the present invention, since the search area setting means specifies the setting value of the search area every block (B+), the setting value of the search area relative to such blocks can be constitutionally changed to broaden the search area when the area could not be specified by the area specifying means relative to some blocks. In such case, the constitution (D+) as described above is not mandatory.

[Action and Effect] The above constitution illustrates another constitution by which the noise reduction image can be acquired absolutely. When the area could not be specified by the area specifying means relative to some blocks, if the setting value of the search area every block on the reference image is specified and the setting value of the search area relative to such blocks is changed to broaden the search area, the area is specified from the broad search area relative to the same block upon the following generation of the noise reduction image so that the incident in which the area corresponding to the block on the reference image cannot be found out can be avoided as much as possible. In this way, the noise reduction fragments can be absolutely acquired from all over the reference image so that the image processing device capable of eliminating further absolutely the noise from the reference image can be provided.

In addition, according to the image processing device having (B+) as described above, it is further preferable that the search area setting means changes the setting value of the search area relative to such blocks so as to narrow the search area when the area could be specified by the area specifying means relative to some blocks,

[Action and Effect] The above constitution illustrates the specific constitution of the image processing device of the present invention. When the area relative to some blocks on the reference image could be specified on the similar image, if the setting value of the search area is changed to narrow the search area relative to such blocks, the area is specified from the narrow search area relative to the same block upon the following generation of the noise reduction image so that the image processing can be sped up.

In addition, the area specifying means of the image processing device according to the present invention specifies the source of the search position on the similar image as the position corresponding to the same position as the block on the reference image (C1), and then by executing the search while changing the search position on the similar image far away from the source, it can be constituted as the area having the same pattern as the pattern of the subject being incorporated in the block of the reference image on the similar image can be specified. In such case, the constitutions (D+), (B+) are not mandatory.

[Action and Effect] The above constitution illustrates another constitution by which the noise reduction image can be acquired absolutely. The source of the search position on the similar image as the position corresponding to the same position as the block on the reference image is specified, and then by executing the search while changing the search position on the similar image far away from the source so that the broader search area will be more operable compared to the search of the limited search area if the area having the same pattern as the pattern of the subject being incorporated in the block of the reference image on the similar image would be specified. In addition, in many cases, the pattern on the similar image, which is the same as the pattern of the subject being incorporated in the block of the reference image, appears near the position corresponding to the block on the similar image. Because the misalignment of the subject images between the reference image and the similar image is deemed not so large. According to the constitution described above, a periphery of the position corresponding to the block on the reference image is preferentially-searched so that the area having the same pattern as the pattern of the subject being incorporated in the block of the reference image can be found out more easily and absolutely. In this way, the noise reduction fragments can be absolutely acquired from all over the reference image so that the image processing device capable of eliminating further absolutely the noise from the reference image can be provided.

In addition, according to the constitution of the image processing device described above, the noise reduction image is repeatedly generated every generation of the frame constituting the live image so that the reference image can be an updated frame constituting the live image and also the constitution in which the similar image imaged just one before the reference image can be adopted.

[Action and Effect] The above constitution illustrates the specific constitution of the image processing device of the present invention. The present invention is applicable when the reference image is an updated frame constituting the live image and also the similar image is the frame imaged just one before the reference image.

In addition, according to the constitution of the image processing device described above, the noise reduction image is repeatedly generated every generation of the frame constituting the live image so that the reference image can be the updated frame constituting the live image and also the constitution in which the similar image is the previously generated noise reduction image can be adopted.

[Action and Effect] The above constitution illustrates the specific constitution of the image processing device of the present invention. The present invention is also applicable when the reference image is the updated frame constituting the live image and also the similar image is the previously generated noise reduction image.

Effect of the Invention

Basically, the image processing device of the present invention is operative to specify the area having the same pattern on the similar image as the pattern of the subject being incorporated into a block of the reference image and repeat multiple times generation of a noise reduction fragment by superimposing the block and the area so that the noise reduction fragments can be acquired all over the reference image and the acquired fragments can be connected to generate the noise reduction image. Eventually, if the image processing device would be operated in such way, the incident in which an area corresponding to the block on the reference image cannot be found out takes place. Thus, the present invention is operative to generate the noise reduction fragments by executing a spatial processing relative to the block. In this way, the noise reduction fragments can be absolutely acquired all over the reference image so that the noise can be further absolutely eliminated from the reference image.

The above and other aspects, features and advantages of the present invention will become apparent from the following description read in conjunction with the accompanying drawings, in which like reference numerals designate the same elements.

BRIEF DESCRIPTION OF THE DRAWINGS

FIG. 3A, 3B are schematic diagrams illustrating a frame of Embodiment 1.

FIG. 6A, 6B are schematic diagrams illustrating an operation of the image processing device of Embodiment 1.

FIG. 10 is a schematic diagram illustrating an operation of the image processing device of Embodiment 1.

FIG. 12 is a schematic diagram illustrating an operation of the image processing device of Embodiment 2.

FIG. 14A, 14B are schematic diagrams illustrating an operation of the image processing device of Embodiment 2.

FIG. 17 is a schematic diagram illustrating an operation of the image processing device of one alternative Embodiment of the present invention.

DETAILED DESCRIPTION OF THE PREFERRED EMBODIMENTS

Figure 1A:
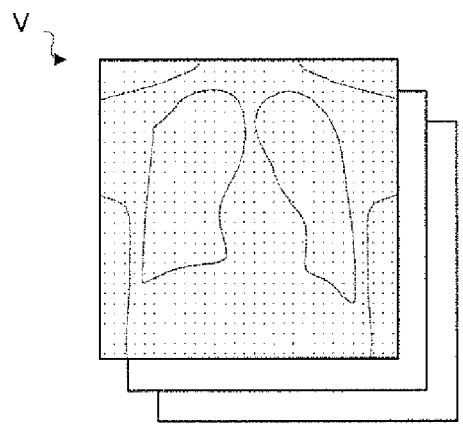
FIG. 1A, 1B are schematic diagrams illustrating the image processing device of Embodiment 1.

Reference will now be made in detail to embodiments of the invention. Wherever possible, same or similar reference numerals are used in the drawings and the description to refer to the same or like parts or steps. The drawings are in simplified form and are not to precise scale. The word 'couple' and similar terms do not necessarily denote direct and immediate connections, but also include connections through intermediate elements or devices. For purposes of convenience and clarity only, directional (up/down, etc.) or motional (forward/back, etc.) terms may be used with respect to the drawings. These and similar directional terms should not be construed to limit the scope in any manner. It will also be understood that other embodiments may be utilized without departing from the scope of the present invention, and that the detailed description is not to be taken in a limiting sense, and that elements may be differently positioned, or otherwise noted as in the appended claims without requirements of the written description being required thereto.

Various operations may be described as multiple discrete operations in turn, in a manner that may be helpful in understanding embodiments of the present invention; however, the order of description should not be construed to imply that these operations are order dependent.

Hereafter, the inventor sets forth the best mode of Embodiment of the present invention.

Embodiment 1

The inventor sets forth Embodiment of the image processing device 10. The image processing device 10 of the present invention is a device that is used to reduce the noise of the live image. The live image imaging is a kind of X-ray imaging and the purpose thereof is to provide imaging with the fluoroscopic images as a video so that the live images can be the video. With regard to such live image imaging, since the subject is exposed to an X-ray for a long time, X-ray dose administered for imaging is controlled relatively lower so as to suppress the radiation exposure dose to the subject. Accordingly, the live image is liable to include a lot of noises because of the inferior S/N ratio thereof.

Figure 1B:
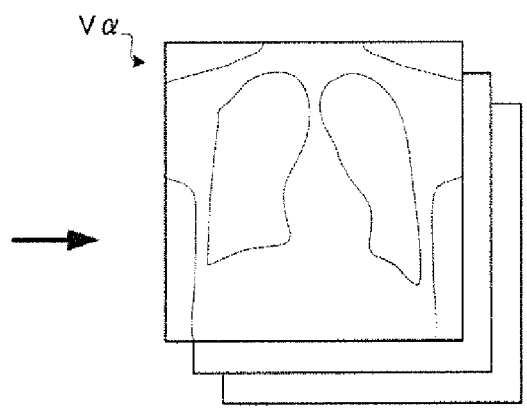

Once the live image V is input to the image processing device 10 of the present invention, referring to FIG. 1, the noise reduction video Vα, of which the noise is reduced, is output from the live image V. Then, the image processing device 10 executes an image processing every frame constituting the live image so that noise can be reduced from each frame and can generate the noise reduction video Vα by connecting the time-series live images in order. The image processing that the image processing device 10 executes is to reduce the noise on the frame by offsetting noises, which appear randomly on each frame, by superimposing a certain frame and the frame imaged one before the certain frame. In such way, the noises illustrated as dot-lines on the live image V in FIG. 1 are reduced so that the noise reduction video Va having an improved visibility can be generated.

Figure 2A:
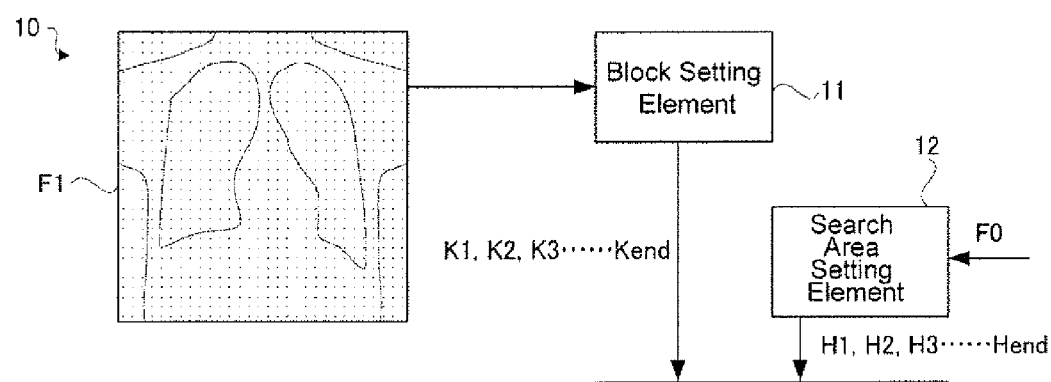
FIG. 2A, 2B are functional block diagrams illustrating the system of the image processing device of Embodiment 1.
Figure 2B:
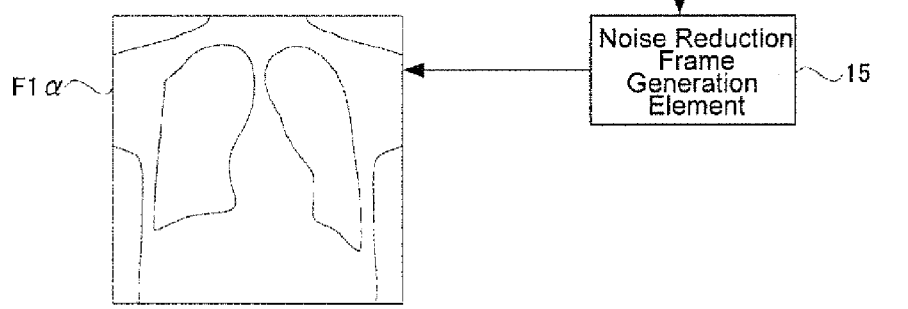

FIG. 2A, 2B are functional block diagrams illustrating the constitution of the image processing device 10. Referring to FIG. 2A, 2B, an image processing device of the present invention comprises; a block setting element 11 that sets up a plurality of blocks K1, K2, K3 . . . Kend on the later imaged frame (frame F1 in FIG. 2A), a search area setting element 12 that sets up the search areas H1, H2, H3 . . . Hend relative to each block on the previously imaged frame (frame F0 in FIG. 2A), an area specifying element 13 that specifies the areas R1, R2, R3 . . . Rend corresponding to the blocks K1, K2, K3 . . . Kend from the search areas H1, H2, H3 . . . Hend, a noise fragment generation element 14 that generates the noise reduction fragments D1, D2, D3 . . . Dend from blocks K1, K2, K3 . . . Kend by superimposing blocks K1, K2, K3 . . . Kend and the corresponding areas R1, R2, R3 . . . Rend thereto; and a noise reduction frame generation element 15 that generates the noise reduction frames (noise reduction frame F1α in FIG. 2B) by connecting the noise reduction fragments D1, D2, D3 . . . Dend each other. Noise incorporated in the frame F1 is illustrated as a shade.

The frame F1 described above corresponds to the reference image of the present invention and frame F0 corresponds to the similar image of the present invention. In addition, the block setting element 11 corresponds to the block setting means of the present invention and the area setting element 12 corresponds to the area setting means of the present invention. And the area specifying element 13 corresponds to the area specifying means of the present invention and the noise reduction fragment generation element 14 corresponds to the noise reduction fragment generation means of the present invention. The noise reduction frame generation element 15 corresponds to the noise reduction image generation means of the present invention.

In addition, FIG. 2 illustrates one Embodiment of the operative image processing based on the frame F1 and the frame F0. The image processing device of the present invention is operative to execute the image processing based on any frame Fm constituting the live image and the frame Fm−1 which is imaged just one before the frame Fm as well as FIG. 2A, 2B.

The inventor briefly sets forth the frame F0 and the frame F1 as illustrated referring to FIG. 2A, 2B. The frame F0 is the first frame acquired once the imaging of the live image begins and the frame F1 is the first frame imaged following the frame F0. Accordingly, the imaging of the frame F0 and the imaging of the frame F1 are time-oriented and adjacent each other.

FIG. 3A, 3B illustrate the frame F0. The frame F0 is the similar image to the frame F1 illustrated in FIG. 2A. With regard to live imaging, since the subject is imaged by a video, the subject image being incorporated in the frame F0 illustrated in FIG. 3B and the image being incorporated in the frame F1 are not exactly the same. This takes place because the subject to be imaged moved between imaging the frame F0 and imaging the following frame F1. The subject image being incorporated in the frame F0 is similar to the subject image being incorporated in the frame F1. The position of the subject being incorporated in the frame F0 is different from the position of the subject being incorporated in the frame F1. Further, the shapes of the subject image being incorporated in each frame F1, F0 are similar but not exactly the same.

In addition, the frame F0 includes the noise as well as in the frame F1. When noise components based on each frame are compared, the appearance pattern thereof is different from each other. Accordingly, it seems that if the frame F0 and the frame F1 are superimposed, the noise component included each frame F0, F1 could be offset and the image having superior visibility could be acquired. However, if the frames F0, F1 are just simply superimposed, referring to FIG. 3B, the subject image incorporated in each frame F0, F1 is superimposed each other with misalignment. Specifically, noise components are certainly offset by superimposition processing but the visibility of the subject image will be tainted.

It is necessary that the subject images should be superimposed with misalignment of the frame F0 every block, which is a small divided block of the frame F1, to suppress such misalignment of the subject upon superimposing the frame F0, F1. Each element 11, 12, 13, 14, 15 is set up for the purpose of bringing such operation into reality. Hereafter, the inventor sets forth the specific operation of each element 11, 12, 13, 14, 15 in order.

[Operation of the Block Setting Element 11]

Figure 4:
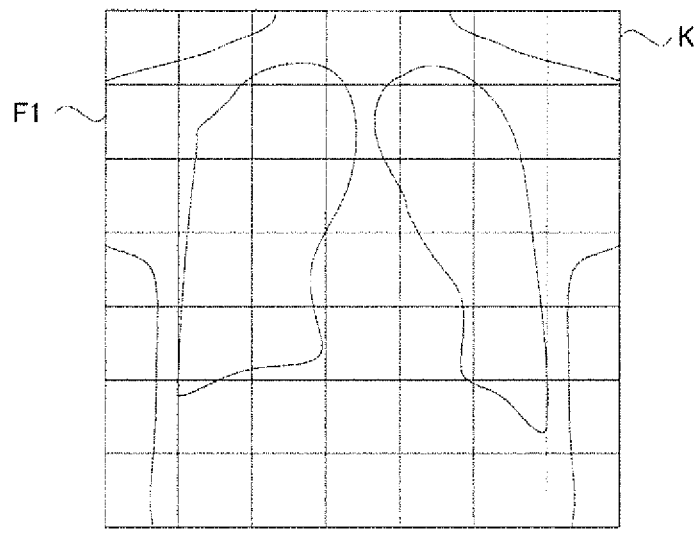
FIG. 4 is a schematic diagram illustrating an operation of the image processing device of Embodiment 1.

FIG. 4 illustrates the operation of the block setting element 11 of Embodiment 1. The block setting element 11 sets up rectangular blocks K1, K2, K3 . . . Kend by dividing the frame F1 imaged later lengthwise and breadthwise. According to the explanation of FIG. 4, for convenience of explanation, the blocks are shown as if tiles without overlapping, but the constitution of Embodiment 1 is not limited thereto and the blocks can be overlapped. Square shape as a shape of the block K can be selected. In such way, the block setting element 11 sets up a part of the frame 1 incorporating the fluoroscopic image of the subject as a block K.

[Operation of the Search Area Setting Element 12]

The positional information of each block K1, K2, K3 . . . Kend set up by the block setting element 11 is output to the search area setting element 12. The search area setting element 12 is operative equally relative to each block K1, K2, K3 . . . Kend. Hereafter, the following explanation illustrates the operation of the search area setting element 12 relative to the block Km among the blocks. The search area is the area that indicates which area of the frame F0 should be searched when the region R1, R2, R3 . . . Rend corresponding to each block K1, K2, K3 . . . Kend is searched out from the frame F0. The region R1, R2, R3 . . . Rend are the regions on the frame F0 that is incorporating the same pattern as the pattern of the subject, being incorporated in each block K1, K2, K3 . . . Kend.

Figure 5A:
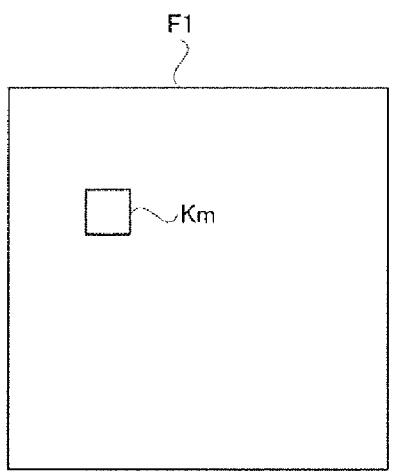
FIG. 5A, 5B are schematic diagrams illustrating an operation of the image processing device of Embodiment 1.
Figure 5B:
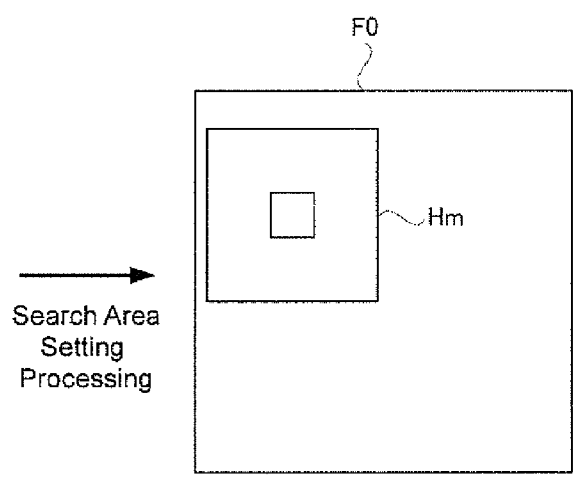

FIG. 5A, 5B illustrate a mode of the search area setting element 12 to set up the search area Hm on the frame F0, corresponding to the block Km. The search area setting element 12 sets up the broader rectangular area than the block Km as the center that is the position corresponding to the block Km on the frame F0. Accordingly, the area is set up on the previous frame F0. Such set area is called as the search area Hm. The search area Hm is corresponding to the block Km.

The extent of the search area Hm is specified by the setting value that the search area setting element 12 holds. In addition, the extent of the search area H1, H2, H3 . . . Hend corresponding to each block K1, K2, K3 . . . Kend is the same as the search area Hm. However, in some cases, relative to the block K in place at the edge of the frame 1, a part of the area, which is set up by the setting value, may be out of the frame F0 so that the search area H can be narrower by an equal extent that is out thereof. The search area setting element 12 outputs the positional information of the search area Hm on the previous frame F0 to the area specifying element 13. In this way, the search area setting element 12 sets up the search area H of the frame F0 on which the position of the subject being incorporated is different from the frame F1.

[Operation of the Area Specifying Element 13]

The positional information of the block Km on the updated frame F1 and the positional information of the search area Hm are output to the area specifying element 13. The area specifying element 13 looks for a pattern similar to the structure of the subject, which is incorporated on the block Km of the frame F1, in the search area Hm of the frame F0. In this way, the area specifying element 13 executes the pattern search in the specified search area so that the search operation can be completed in a short period of time.

FIG. 6A, 6B illustrate the pattern matching operation that is executed by the area specifying element 13. The area specifying element 13 acquires the average value of the pixel values of the pixels constituting the block Km as illustrated in FIG. 6A. Then, the area specifying element 13 notices the rectangular region that has the same shape and size as the block Km belonging to the search area Hm and acquires the average value of the pixel values of the pixels constituting the region thereof. Then, the area specifying element 13 acquires the average values one right after the other while changing the position of the region on the search area Hm. FIG. 6B illustrates the mode in which a plurality of the average values are being acquired while the region shifts from the top end of the left side to the bottom end of the right side on the search area Hm.

The area specifying element 13 selects the region having the closest average value to the average of the block Km from each region and specifies this region as the region that is the pattern thereof similar to the structure of the subject which is incorporated on the block Km. When specifying, the area specifying element 13 utilizes the principle as the average value of the block Km and the average value of the instant region are similar if the pattern of the block Km and the pattern of the region are similar each other. The block Km should include the noise component but the noise component included in the block Km can be offset when the average value is calculated. Accordingly, the average value could not be disturbed by the noise component. In such circumstances, the region on the search area Hai is deemed as the same so that the comparison of each average value cannot be affected by the noise component. Thus, the area specifying element 13 specifies the area R having the same pattern as the pattern of the subject being incorporated in the block Km of the frame F1 on the frame F0 by searching in the search area of the frame F0.

Further, according to the above description, the area specifying element 13 executes the pattern matching by using the average value as a benchmark, Embodiment is not limited to the above constitution and other benchmarks such as a histogram and so forth can be employed.

Figure 7A:
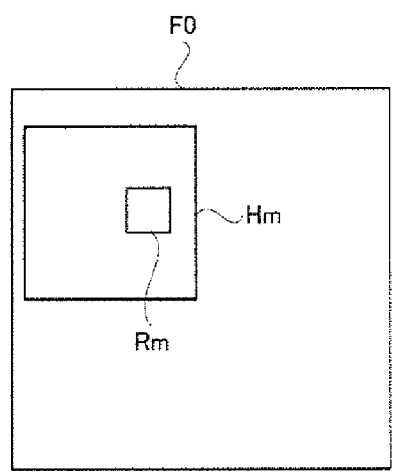
FIG. 7A, 7B are schematic diagrams illustrating an operation of the image processing device of Embodiment 1.
Figure 7B:
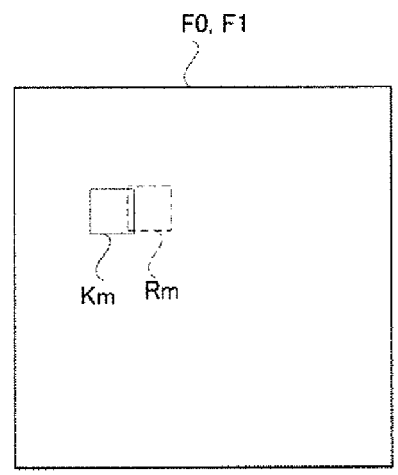

Referring to FIG. 7A, it is assumed that the area specifying element 13 specified that the area Rm, one of each region on the search area Elm is incorporating the similar pattern to the block Km. FIG. 7B is the superimposed view of the frame F0, F1. According to this FIG., the position of the block Km and the position of the area Rm are out of alignment each other in the lateral direction. The misalignment in the lateral direction takes place because the subject moved between imaging the frame F0 and imaging the following frame F1. Further, the misalignment in the lateral direction is restricted to the block Km and it does not automatically mean that the other block K on the frame F1 is also out of alignment.

[Operation of the Noise Reduction Fragment Generation Element 14: In the Case of That the Area Rm Corresponding to the Block Km Exists.]

Figure 8A:
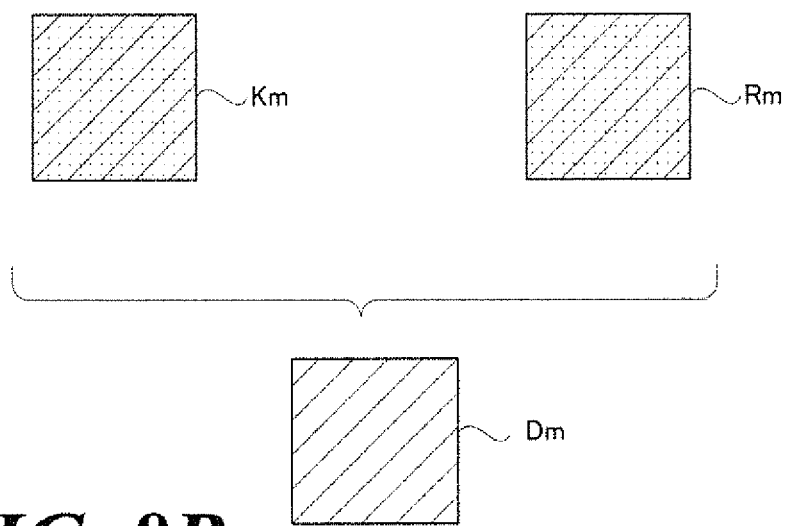
FIG. 8A, 8B are schematic diagrams illustrating an operation of the image processing device of Embodiment 1.

The positional information of the block Km on the updated frame F1 and the positional information of the search area Rm on the previous frame F0 are output to the noise reduction fragment generation element 14. Referring to FIG. 8A, the noise reduction fragment generation element 14 adds the image on the block Km and the image on the area Rm while weighing so that the noise reduction fragment Dm, in which the noise of the block Km is reduced, can be generated.

The inventor sets forth the principle by which the noise of the block Km is reduced in such operation. The block Km and the area Rm are images as if the noise component is superimposed on the pattern due to the structure of the subject. The pattern incorporated in the block Km and the pattern incorporated in the area Rm are similar each other so that such pattern cannot be offset by the superimposition processing and can appear on the noise reduction fragment Dm. On the other hand, the noise component incorporated in the block Km and the noise component incorporated in the area Rm are not similar each other. The noise component is always fluctuating so that the incorporation mode is different from one imaging to another imaging. Accordingly, the noise component is offset each other by superimposition processing so that it can most unlikely appear on the noise reduction fragment Dm. In this way, the noise reduction fragment generation element 14 generates the noise reduction fragment D, wherein the noise components incorporated in the block Km and the area Rm are offset each other by superimposing the area R on the frame F0 and the block K on the frame F1, which are specified by the area specifying element 13.

[Operation of the Noise Reduction Fragment Generation Element 14: In the Case of that the Area Rm Corresponding to the Block Km does not Exist.]

According to the constitution of Embodiment 1, if no area Rm corresponding to the block Km exists, it is considered that how the noise reduction fragment generation element 14 is operative. This operation is unique and not found in the conventional constitution. It is not guaranteed whether the area Rm corresponding to the block Km can be found by the operation of the area specifying element 13. An example in which the area could not be found, for example, may include the case in which the pattern similar to the structure of the subject incorporated in the block Km on the frame F1 exists outside the search area Hm on the frame F0, or the instant pattern is outside the frame when the frame F0 is imaged, because the move of the subject is too heady when the frame F0, F1 are imaged.

Figure 8B:
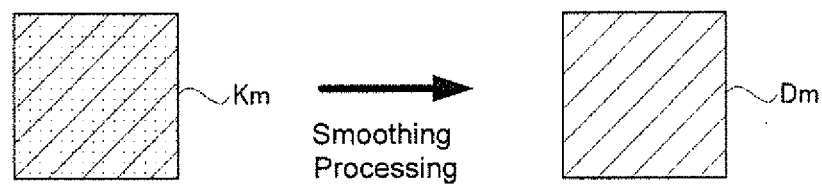

When the area Rm corresponding to the block Km is not found, the area specifying element 13 outputs the signal indicating that the area Rm was not found to the noise reduction fragment generation element 14 instead of the positional information of the area Rm. Based on this signal, the noise reduction fragment generation element 14 generates the noise reduction fragment Dm only by the block Km. Specifically, referring to FIG. 8B, the noise reduction fragment generation element 14 executes smoothing processing relative to the block Km and specifies the result as the noise reduction fragment Dm. Such generation method of the noise reduction fragment Dm obfuscates the structure incorporated in the block Km. Accordingly, if the superimposition operation, as described in FIG. 8A, rather than such operation, is preferentially-executed, the clearer noise reduction fragment Dm inclines toward being acquired.

The data that defines the image of the noise reduction fragments Dm acquired by any methods described above is output to the noise reduction frame generation element 15 with the positional information relative to the frame F1. In this way, the noise reduction fragment generation element 14 generates the noise reduction fragment D by executing the spatial processing relative to the block K when the area specifying element 13 fails specify the area R.

[Repeat Operation of Each Element 11, 12, 13, 14]

The operation of each element 11, 12, 13, 14 described above is as to one of the blocks K constituting the frame F1. Each element 11, 12, 13, 14 generates the noise reduction fragment D1, D2, D3 . . . Dend relative to all blocks K1, K2, K3 . . . Kend constituting the frame F1. These noise reduction fragment D1, D2, D3 . . . . Dend includes one generated by superimposing the block K and the corresponding area R thereto and another one generated by smoothing processing the block K. The noise reduction fragment element 14 outputs the data that defines the generated noise reduction fragment D1, D2, D3 . . . Dend to the noise reduction frame generation element 15 with the positional information relative to the frame F1.

[Operation of the Noise Reduction Frame Generation 15]

Figure 9:
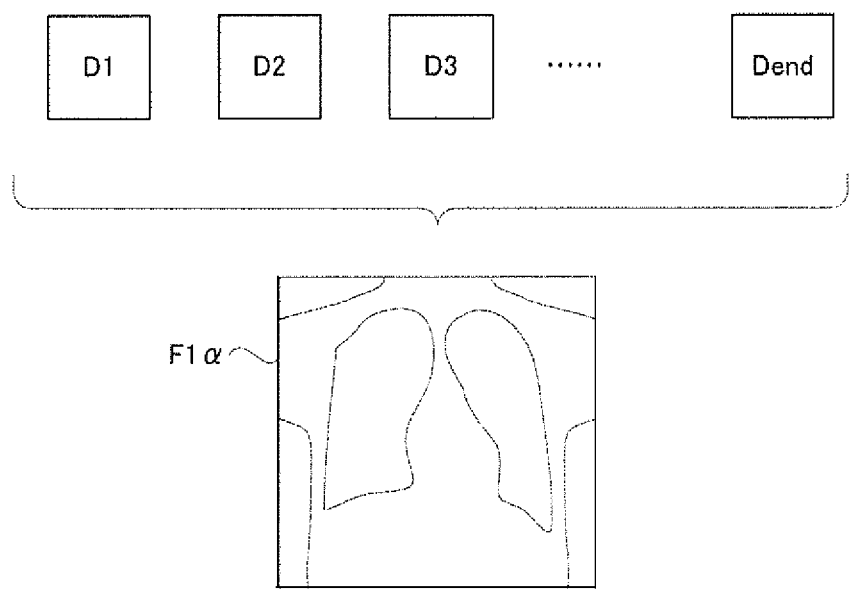
FIG. 9 is a schematic diagram illustrating an operation of the image processing device of Embodiment 1.

The noise reduction frame generation element 15, referring to FIG. 9, arranges and then connects the noise reduction fragments Dm according to the attached positional information to generate the noise reduction frame F1α. The noise reduction frame F1α is an image as if the noise component is reduced from the frame F1. In this way, the noise reduction frame generation element 15 generates the noise reduction frame F1α, wherein the noise component being incorporated in the frame F1 by connecting the noise reduction fragments D relative to each block K that is set up by the block setting element 11 over the frame F1.

[Repeat of the Noise Reduction Frame Generation]

The above description sets forth the operation by which the noise reduction frame F1α relative to the frame F1 is generated. The image processing device 10 is also operative to execute as for other frame F2 and to generate the noise reduction frame Fα corresponding thereto one right after the other. FIG. 10 illustrates the mode in which the image processing device 10 generates continuously the noise reduction frame Fα in accordance with generation of the frame F one right after the other. Specifically, with regards to imaging the live image V, when the X-ray radiographic device images the frame F1, the image processing device 10 that receives the frame F1 generates the noise reduction frame F1α based on the frame F0, F1, and when the X-ray radiographic device images the frame F2, the image processing device 10 that receives the frame F2 generates the noise reduction frame F2α based on the frame F1, F2.

Then after, when the X-ray radiographic device images the frame Fn, the image processing device 10 that receives the frame Fn generates the noise reduction frame Fnα based on the frame Fn−1, Fn. Specifically, the image processing device 10 is the device that is capable of executing in real time the noise reduction in accordance with imaging of the live image V. Further, the operation of the image processing device 10 to generate the noise reduction frame F1α is called as the first operation and the operation of the image processing device 10 to generate the noise reduction frame F2α is called as the second operation. Then after, the operation of the image processing device 10 to generate the noise reduction frame Fnα is called as the number N operation.

According to Embodiment 1, the image processing device 10 comprise the constitution in which the noise reduction frame F1α is repeatedly generated every generation of the frame constituting the live image by the X-ray radiographic device so that the frame F1 divided by the block K is the updated frame constituting the live image and also the frame F0 in which the pattern search that is the same as the block K is executed is the frame imaged just one before the frame 1.

At this time, if the noise reduction frame Fα is displayed one right after the other in accordance with the generation order, the live image V, as if the noise components thereof is reduced, can be displayed in real time. However, there is a time lag in some extent from when the frame Fn is generated until when the noise reduction frame Fnα is generated. Referring to FIG. 1, the live image, relative to the noise reduction, displayed on the monitor at this time is represented as the noise reduction video Vα.

Figure 11:
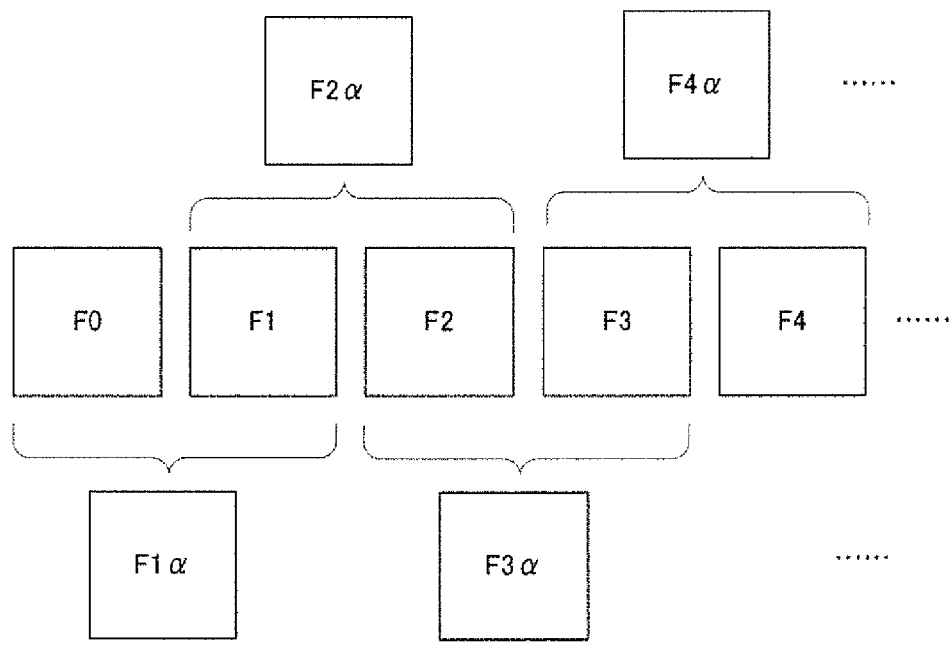
FIG. 11 is a schematic diagram illustrating an operation of the image processing device of Embodiment 1.

FIG. 11 schematically represents the mode in which the image processing device 10 generates the noise reduction frame Fα one right after the other in accordance with the imaging the frame F. The image processing device 10 generates the noise reduction frame by using the updated frame and the frame imaged once before the updated frame.

Accordingly, the image processing device 10 of the present invention is operative to specify the area R having the same pattern as the pattern of the subject being incorporated into the block K on the frame F1 and to repeat multiple times generation of a noise reduction fragment D by superimposing the block K and the area R so that it is basically operative to acquire each noise reduction fragment D1, D2, D3 . . . Dend all over the frame F1 and to connect the acquired fragments to generate the noise reduction frame F1α. Eventually, if the image processing device 10 would be operated in such way, the incident in which an area R corresponding to the block K on the frame F1 cannot be found out takes place. Thus, the present invention is operative to generate the noise reduction fragments D by executing a spatial processing relative to the block K when the area R having the same as the pattern of the subject being incorporated into a block K on the frame F1 cannot be found out on the frame F0. In this way, the noise reduction fragments D can be absolutely acquired all over the frame F1 so that the image processing device 10 capable of eliminating further absolutely noise from the frame F1 can be provided.

Embodiment 2

Next, the inventor sets forth a constitution of the image processing device 10 according to Embodiment 2. The image processing device 10 of Embodiment 2 is almost the same as the device of Embodiment 1. According to the device of Embodiment 1, the extent of search areas is constant relative to all frames F1, F2, F3 . . . Fend, but the extent of the search areas relative to the image processing device 10 of Embodiment 2 can be optimized in accordance with generation of the noise reduction frame Fα. Specifically, since the search area setting element 12 specifies the setting value of the search area H every block, the setting value of the search area H can be changed to broaden the search area H relative to the block K when the area specifying element 13 would fail to specify the search area R relative to some block K. In addition, the search area setting element 12 changes the setting value of the search area H relative to such block K so as to narrow the search area H when the area specifying element 13 would succeed to specify the search area R relative to some block K. Hereafter, the inventor sets forth the specific constitution of the search area setting element 12.

Figure 12:
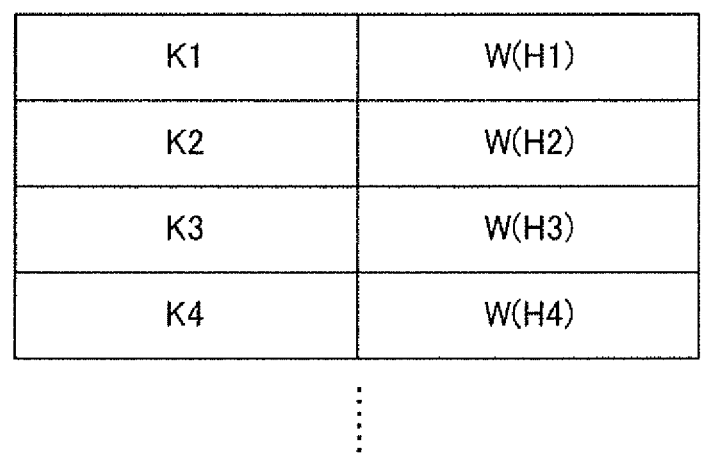

The search area setting element 12 executes the extent adjustment of the search area H every each block K1, K2, K3 . . . Kend. FIG. 12 is a table showing the corresponding relationship between each block K1, K2, K3 . . . Kend and the setting value W(H1), W(H2), W(H3) . . . W(Hend) of the extent of the search area H1, H2, H3 . . . Hend corresponding thereto. The search area setting element 12, which has the table, refers the table to recognize the extent of the search area H when setting the search area H on the frame F. Further, each setting value W(H1), W(H2), W(H3) . . . W(Hend) can be the same as the value in the initial state prior to generation of a series of the noise reduction frames F1α, F2α, F3α . . . Fendα. In this case, the image processing device 10 of Embodiment 2 is operative to execute the same as the operation in the device of Embodiment 1 thereon when executing the first noise reduction frame generation operation.

According to the constitution of Embodiment 2, the inventor sets forth the mode of the constitution in which each setting value W(H1), W(H2), W(H3) . . . W(Hend) in the table of FIG. 12 is being rewritten following repeated generation of the noise reduction frame Fα.

Figure 13:
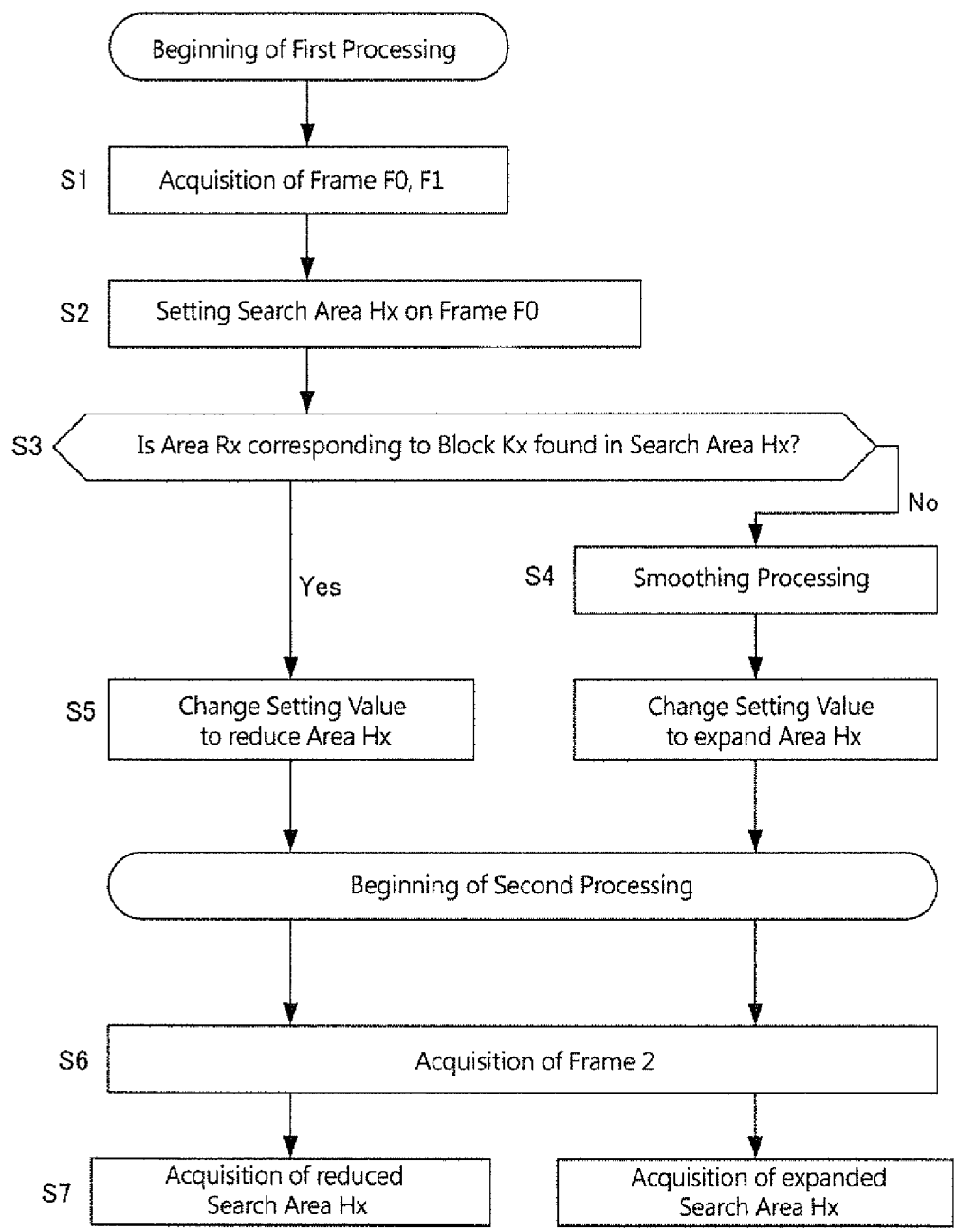
FIG. 13 is a schematic diagram illustrating an operation of the image processing device of Embodiment 2.

FIG. 13 illustrates the operation of the image processing device 10 with regard to repeated generation of the noise reduction frame Fα. FIG. 13 illustrates the first processing relative to the noise reduction frame F1α and the second processing relative to the noise reduction frame F2α, but the image processing device 10 of Embodiment 2 is operative to execute the same as even when generating other noise reduction frames Fα.

When the image processing device 10 executes the first processing, according to the step S1 of FIG. 13, the frame F0, F1 are firstly acquired from the X-ray radiographic device. And, according to the step S2, the search area H, corresponding to each block K on the frame F1, on the frame F0 is set up. Further, relative to the step S2, the inventor sets forth the case in which the search area Hx corresponding to a certain block Kx among a plurality of settings of the search area H is set up. The search area setting element 12 decides the extent of the search area Hx by referring to the table set forth as to FIG. 12. Further, such operation is executed by the search area setting element 12 relative to each block K1, K2, K3 . . . Kend.

Without interruption, the area specifying element 13 begins the operation to search the same pattern as the pattern of the structure of the subject, being incorporated in the block Kx, from the search area Hx. At this time, there is the case in which the area Rx including the same pattern as the block Kx could be found out or the case in which it could not be found out. When the area Rx is found out, the area Rx is output to the noise reduction fragment generation element 14 so as to utilize for the noise reduction of the block Kx. On the other hand, when the area Rx is not found out, the noise reduction fragment generation element 14 executes the smoothing processing relative to the block Kx (refer to the step S4.) Such operation of the image processing device 10 is the same as the operation set forth in Embodiment 1.

[Characteristic Constitution Relative to Embodiment 2]

The following operation is most characteristic of the image processing device 10 of Embodiment 2. Specifically, the search area setting element 12 changes the extent of the search area Hx toward reduction of the search area Hx when the area Rx is found out (refer to step S5.) Such change is specifically executed by changing the setting value relative to the search area Fix in the table that the search area setting element 12 has.

The specific reduction level of the search area Hx is not limited, but, for example referring to FIG. 14A, 14B, the method so as to change the setting value until the rectangular search area Hx is reduced to let the area Rx move to the edge of the area can be considered. The setting value is only just a parameter relative to the extent of the search area Hx so that the center position c of the search area Hx on the frame F1 would not change, even if the setting value would change. The center c coincides with the center position of the block Kx.

On the other hand, the search area setting element 12 changes the extent of the search area Hx toward expansion of the search area Hx when the area Rx is not found out (refer to step S5.) Such change is specifically executed by changing the setting value relative to the search area Hx in the table that the search area setting element 12 has. The specific expansion level of the search area Hx is not particularly limited, but, for example, the method so as to change the setting value until the rectangular search area Hx is expanded as much as double width of block Kx can be considered. The setting value is only just a parameter relative to the extent of the search area Hx so that the center position c of the search area Hx on the frame F1 would not change, even if the setting value would change. The center c coincides with the center position of the block Kx.

The search area setting element 12 executes to change the extent of such search area H as well as each search area H1, H2, H3 . . . Hend.

In this way, since the setting value defining the extent of each search area H is changed, the image processing device 10 finally begins the second processing (generation processing of the noise reduction frame F2α.) However, referring to FIG. 13, when the image processing device 10 executes the second processing, the frame F2 is first acquired from the X-ray radiographic device according to the step S1. And, according to the step S7, the search area Hx on the frame F1 corresponding to the block Kx on the frame F2 is set up. At this time, the setting value defining the extent of the search area Hx is changed in accordance with step S5. Specifically, when the second processing sets up the search area Hx, if the search area Rx is found out during step S3 of the first processing, the narrower search area Hx than at the first time is set up on the frame F2. Even if such narrower search area is set up, it is deemed that the area Rx can be found out despite the second processing. Because the move level of the subject relative to the specific region is deemed as the same as the level throughout each frame F. The high speed image processing can be brought into reality by narrowing the search area Hx.

On the other hand, when the second processing sets up the search area Hx, if the search area Rx could not be found out during step S3 of the first processing, the broader search area Hx than at the first time is set up on the frame F2. Even if such broader search area is set up, the area Rx could be easily found out in the second processing. If the area R were found out, the noise reduction fragment D incorporating the clearer subject image can be generated. Accordingly, the change so as to broaden the search area Hx contributes to improve quality of the image of the noise reduction frame Fα.

The search area setting element 12 executes setting such search area H as well as each search area H1, H2, H3 . . . Hend. The extent of the search area H1, H2, H3 . . . Hend may increase or decrease following a number of image processings. Accordingly, the search area H would not broaden unlimitedly while continuing the image processing. Characteristics of such constitution of Embodiment 2 contribute to speed-up of the image processing.

The above constitution of Embodiment 2 illustrates another different constitution from Embodiment 1 by which the noise reduction frame F1 a can be absolutely acquired. Specifically, when the area R could not be specified by the area specifying element 13 relative to some blocks K, if the setting value of the search area H every block K on the frame F1 is set and the setting value of the search area H relative to such block K is changed to broaden the search area H; when the following generation of the noise reduction fragment frame F1; the area R is specified from the broad search area H relative to the same block K so that the incident in which the area R corresponding to the block K on the frame F1 cannot be found from the frame F0 out can be avoided as much as possible. In this way, the noise reduction fragments D can be absolutely acquired all over the frame F1 so that the image processing device 10 capable of eliminating further absolutely noise from the frame F1 can be provided.

In addition, as described above, when the area R could be specified on the frame F0 relative to some blocks K on the frame F1, if the setting value of the search area H is changed to narrow the search area H relative to such block K; when the following generation of the noise reduction frame F1α; the area R is specified from the narrow search area H relative to the same block K so that the image processing can be sped up.

The present invention is not limited to the above constitution and further following alternative Embodiment can be implemented.

(1) According to the above Embodiments, the constitution is as the pattern of each block K1, K2, K3 . . . Kend is searched from the limited search area H1, H2, H3 . . . Hend, but the present invention is not limited to such constitution. The constitution of the present invention may be as the same pattern as the block K on the frame F1 is searched from a broad area of the frame F0.

Figure 15A:
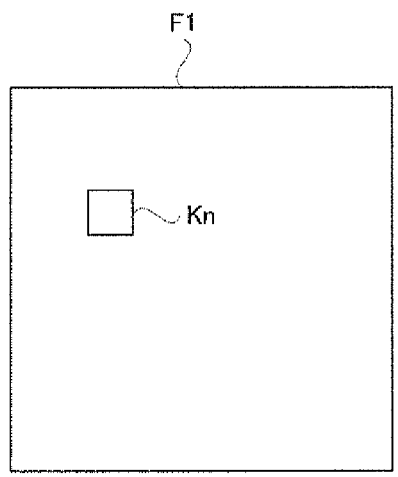
FIG. 15A, 15B are schematic diagrams illustrating an operation of the image processing device of one alternative Embodiment of the present invention.
Figure 15B:
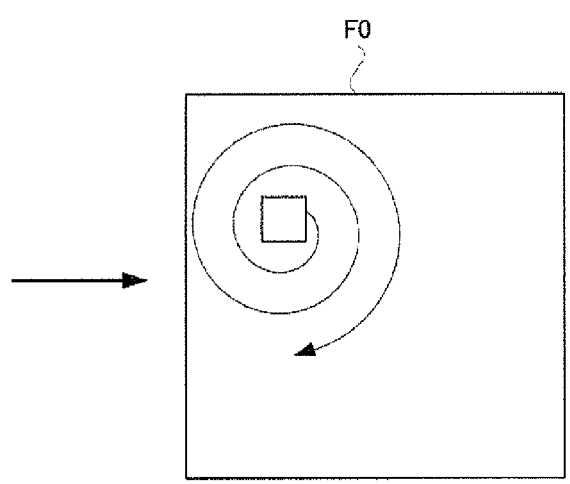
Figure 16:
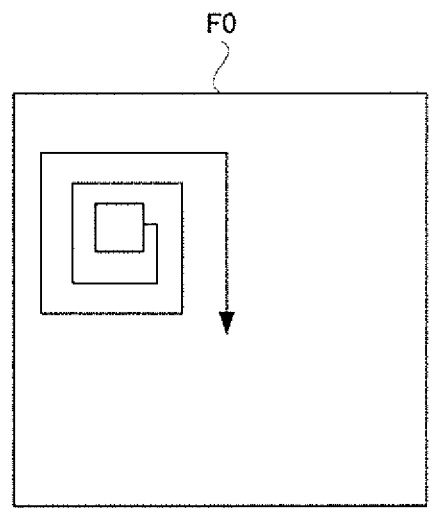
FIG. 16 is a schematic diagram illustrating an operation of the image processing device of one alternative Embodiment of the present invention.

Specifically, referring to FIG. 15A, 15B, the pattern matching can be executed while moving the search target region gradually away from the source, wherein the search target region on the frame F0 is the source that is the position corresponding to the block Kn on the frame F1. Referring to FIG. 15A, 15B, for example, the constitution in which the spiral trail can be followed can be adopted as the direction to move the search target region. Further, referring to FIG. 16, as the other direction to move the search target region, the instant region can be moved to follow the spiral trail acquired by connecting orthogonally-crossed line each other while repeating the move operation in the longitudinal direction of the frame F0 and then the move operation in the lateral direction.

In this way, the area specifying element 13 specifies the source of the search position as the position corresponding to the same position as the block K on the frame F1, and then by executing the search while changing the search position on the frame F0 away from the source, the area R having the same pattern as the pattern of the subject being incorporated in the block K of the frame 1 on the frame F0 is specified.

In addition, even relative to the present alternative Embodiment, the case in which the area R corresponding to the block K could not be found takes place. Such phenomenon takes place when the region corresponding to the block K on the frame F1 is out of the frame while imaging. In this case, in accordance with Embodiment 1, the noise reduction fragment generation element 14 acquires the noise reduction fragment D by adding the smoothing processing on the block K.

The present alternative Embodiment illustrates a different constitution from Embodiment 1, 2 by which the noise reduction frame image F1 α can be absolutely acquired. The source of the search position on the frame F0 as the position corresponding to the same position as the block K on the frame F1 is specified, and then if the area R having the same pattern as the pattern of the subject being incorporated in the block K of the frame F1 on the frame F0 would be specified by executing search while changing the search position on the frame F0 away from the source, the broader area search would be operable compared to searching the area R in the limited search area H.

In addition, in many cases, the pattern on the frame F0, which is the same as the pattern of the subject being incorporated on the block K of the frame F1, appears near the position corresponding to the block K on the frame F0. Because the misalignment of the subject images between the frame F1 and the frame F0 is deemed not so large. According to the constitution described above, if a periphery of the position corresponding to the block K on the frame F0 is preferentially-searched, the area R having the same pattern as the pattern of the subject being incorporated in the block K of the frame F1 can be found out more easily and absolutely. In this way, the noise reduction fragments D can be absolutely acquired all over the frame F1 so that the image processing device 10 capable of eliminating further absolutely noise from the frame F1 can be provided.

(2) According to Embodiments as described above, the constitution is that two frames F are superimposed each other to generate the noise reduction frame Fα but the present invention is not limited to such constitution. Referring to FIG. 17, the noise reduction frame Fα can be the integral image of the frame F0, F1, F2, F3 . . . . According to the image processing device 10 of the present alternative Embodiment, the first-time processing is the same as the processing in Embodiment as described above. The noise reduction frame S1α referring to FIG. 17 is the same as the noise reduction frame F1α set forth in Embodiment 1.

According to the present alternative Embodiment, in the second-time processing, the noise reduction frame S2α is generated by superimposing the noise reduction frame S1α and the frame F2. At this time, the frame F2 is divided to each block K1, K2, K3 . . . Kend, the noise reduction fragment D1, D2, D3 . . . Dend is generated by searching the area R1, R2, R3 . . . Rend corresponding thereto from the noise reduction frame S1α and then the connecting operation thereof is conducted. The frame F2 described above corresponds to the reference image of the present invention and the noise reduction frame S1α corresponds to the similar image of the present invention.

According to the present alternative Embodiment, in the third-time processing, the noise reduction frame S3α is generated by superimposing the noise reduction frame S2α and the frame F3. At this time, the frame F3 is divided to each block K1, K2, K3 . . . Kend, the noise reduction fragment D1, D2, D3 . . . Dend is generated by searching the area R1, R2, R3 . . . Rend corresponding thereto from the noise reduction frame S2α and then the connecting these becomes operable.

Since, according to the present alternative Embodiment, in the N-time processing, the noise reduction frame Snα is generated by superimposing the noise reduction frame Sn−1α and the frame Fn. At this time, the frame Fn is divided to each block K1, K2, K3 . . . Kend, the noise reduction fragment D1, D2, D3 . . . Dend is generated by searching the area R1, R2, R3 . . . Rend corresponding thereto from the noise reduction frame Sn−1α and then the connecting operation thereof is conducted. The image processing device 10 according to the present alternative Embodiment has the constitution in which the noise reduction frame Fα is repeatedly generated every generation of the frame constituting the live image by the X-ray radiographic device so that the updated frame constituting the live image is divided to the block K and also the search for the same pattern as the block K is executed relative to the previously generated noise reduction frame Fα.

(3) According to Embodiments as described above, when the area R corresponding to the block K on the frame F1 could not be found out from the frame F0, the noise reduction fragment D is generated by smoothing processing on the block K, but the present invention is not limited to such constitution. Specifically, the present invention can adopt the constitution in which the noise reduction fragment D is generated by executing the spatial processing other than the smoothing processing relative to the block K. The spatial processing other than the smoothing processing may include, e.g., a median image processing and so forth.

(4) The constitution of the image processing device of the present invention may have one or all of Embodiment 1. Embodiment 2 and the alternative Embodiment as described above unless otherwise such constitution becomes contradictory.

INDUSTRIAL APPLICABILITY

As set forth above, the image processing device of the present invention is suitable for medicinal field.

REFERENCE OF SIGNS

D Noise reduction fragment
F1 Frame (Reference image)
F0 Frame (Similar image)
F1α Noise reduction image
H Retrieval range
K Block
R Area
11 Block setting element (Block setting means)
12 Search area setting element (Search area setting means)
13 Area specifying element (Area specifying means)
14 Noise reduction fragment generation element (Noise reduction fragment generation means)
15 Noise reduction frame generation element (Noise reduction image generation element)

Having described at least one of the preferred embodiments of the present invention with reference to the accompanying drawings, it will be apparent to those skills that the invention is not limited to those precise embodiments, and that various modifications and variations can be made in the presently disclosed system without departing from the scope or spirit of the invention. Thus, it is intended that the present disclosure cover modifications and variations of this disclosure provided they come within the scope of the appended claims and their equivalents.

What is claimed is:

1. An image processing device, comprising:
(A) a block setting circuit module that operably sets a part of a reference image incorporating a fluoroscopic image of a subject as a block;
(B) a search area setting circuit module that operably sets up a search area in a similar image, wherein a position of said subject being incorporated is different from the position thereof in said reference image;
(C) a area specifying circuit module that operably specifies an area having a same pattern on said similar image as a pattern of the subject being incorporated in said block of said reference image;
(D) a noise reduction fragment generation circuit module that operably generates a noise reduction fragment, wherein noise components incorporated in said block and said area are offset from each other by superimposing the area on said similar image that is specified by said area specifying circuit module and said block of said reference image; and
(E) a noise reduction image generation circuit module that operably generates a noise reduction image, wherein a noise being incorporated in said reference image is reduced by connecting said noise reduction fragment relative to each block that said block setting circuit module sets up all over said reference image; and
wherein (D+) said noise reduction fragment generation circuit module generates said noise reduction fragment by operably executing a spatial processing relative to said block when said area specifying circuit module fails to specify said area.

2. The image processing device, according to claim 1, wherein:
the spatial processing executed by said noise reduction fragment generation circuit module is a smoothing processing.

3. An image processing device, comprising:
(A) a block setting circuit module that sets a part of a reference image operably incorporating a fluoroscopic image of a subject as a block;
(B) a search area setting circuit module that operably sets up a search area in a similar image, wherein a position of the subject being incorporated is different from a position thereof in said reference image;
(C) an area specifying circuit module that operably specifies an area having a same pattern on said similar image as a pattern of the subject being incorporated in said block of said reference image;
(D) a noise reduction fragment generation circuit module that operably generates a noise reduction fragment, wherein a plurality of noise components operably incorporated in said block and said area are operably offset each other by superimposing said area on said similar image that is specified by said area specifying circuit module and said block of said reference image; and
(E) a noise reduction image generation circuit module that operably generates a noise reduction image, wherein a noise being incorporated in said reference image is operably reduced by connecting said noise reduction fragment relative to each block that said block setting circuit module sets up all over said reference image; and wherein (B+) said search area setting circuit module operably specifies a setting value for said search area every said block, and wherein the setting value for said search area relative to some blocks can be operably changed to broaden said search area when said area specifying circuit module fails to specify said area relative to some blocks.

4. An image processing device, according to claim 3 comprising:

said search area setting circuit module operably changes the setting value of said search area relative to such blocks so as to narrow said search area when said area specifying circuit module could operably specify the area relative to some blocks.

5. An image processing device, comprising:

(A) a block setting circuit module that operably sets up a part of a reference image incorporating a fluoroscopic image of a subject as a block;

(C1) a area specifying circuit module that operably specifies an area having a same pattern as a pattern of the subject being operably incorporated on said block of said reference image on a similar image by operably executing a search while changing a search position on said similar image away from a source, wherein the source of the search position on said similar image, having a different position of the subject being incorporated from said reference image, is specified as a position corresponding to a same position as said block on said reference image;

(D) a noise reduction fragment generation circuit module that operably generates a noise reduction fragment, wherein a plurality of noise components operably incorporated in said block and said area are operably offset from each other by superimposing said area on said similar image that is specified by said area specifying circuit module and said block of said reference image; and (E) a noise reduction image generation circuit module that operably generates a noise reduction image, wherein the noise components being incorporated in the reference image are reduced by connecting said noise reduction fragment relative to each block that the block setting circuit module sets all over the reference image.

6. The image processing device, according to claim 1 comprising;

a construction, wherein said noise reduction image is repeatedly generated at every generation of a frame construction a live image; and said reference image is an updated frame constituting the live image, and also said similar image is the frame imaged just one before said reference image.

7. The image processing device, according to claim 1 comprising:

a construction, wherein said noise reduction image is repeatedly generated at every generation of a frame constituting a live image; and wherein said reference image is an updated frame constituting the live image and also said similar image is the noise reduction image previously generated.

* * * * *